United States Patent [19]
Wilmott et al.

[11] Patent Number: 4,826,828
[45] Date of Patent: May 2, 1989

[54] COMPOSITION AND METHOD FOR REDUCING WRINKLES

[75] Inventors: James M. Wilmott, West Milford, N.J.; Alexander P. Znaiden, Sloatsburgh, N.Y.

[73] Assignee: Avon Products, Inc., New York, N.Y.

[21] Appl. No.: 948,361

[22] PCT Filed: Apr. 17, 1986

[86] PCT No.: PCT/US86/00780

§ 371 Date: Dec. 15, 1986

§ 102(e) Date: Dec. 15, 1986

[87] PCT Pub. No.: WO86/06275

PCT Pub. Date: Nov. 6, 1986

Related U.S. Application Data

[63] Continuation-in-part of Ser. No. 845,256, Mar. 28, 1986, abandoned, which is a continuation-in-part of Ser. No. 725,480, Apr. 22, 1985, abandoned, which is a continuation-in-part of Ser. No. 702,328, Feb. 15, 1985, abandoned.

[51] Int. Cl.$^4$ .................. A61K 31/07; A61K 31/695
[52] U.S. Cl. ........................................ 514/63; 514/725
[58] Field of Search .................................. 514/63, 725

[56] References Cited

U.S. PATENT DOCUMENTS

| | | | |
|---|---|---|---|
| 4,224,319 | 9/1980 | Marcadet | 424/238 |
| 4,423,041 | 12/1983 | Clum et al. | 424/184 |
| 4,425,364 | 1/1984 | Vanlerberghe et al. | 424/358 |

OTHER PUBLICATIONS

Kligman et al, J. of Invest. Derm., 73, 354–358, 1979.

*Primary Examiner*—Leonard Schenkman
*Attorney, Agent, or Firm*—S. Michael Bender

[57] ABSTRACT

Stable retinol compositions are disclosed. The compositions comprise retinol, a volatile silicone and a mutual solvent for the retinol and silicone. Preferred compositions contain retinol, cyclomethicone and ethanol.

Were the retinol level in the compositions is between 0.005 and 1.0 weight percent, the compositions may be topically applied to the skin in areas where fine lines, wrinkles or other signs of aging exist. Such topical application results in a reduction in wrinkles and fine lines and improves skin quality. Where the compositions contain more than 0.005 to 1.0 weight percent retinol they may be diluted with cosmetically acceptable carriers or vehicles, preferably water in oil emulsions to reduce the retinol level and topically applied.

10 Claims, No Drawings

COMPOSITION AND METHOD FOR REDUCING WRINKLES

This application is a contination-in-part of prior copending U.S. application Ser. No. 845,256, filed Mar. 28, 1986, which, in turn, is a continuation-in-part of prior copending U.S. application Ser. No. 725,480 filed Apr. 22. 1985, which, in turn, is a continuation-in-part of prior U.S. application Ser. No. 702,328, filed Feb. 15, 1985, all now abandoned.

BACKGROUND OF THE INVENTION (a) Field of the Invention

This invention relates to stable compositions containing retinol which upon topical application to the skin cause wrinkle effacement and other beneficial effects. It also relates to use of such compositions in combination with or including moisturizers.

(b) State of the Art

Retinol (Vitamin A), though believed to cause beneficial skin effects, has never been successfully formulated in a composition suitable for topical application. It has now been discovered that retinol can be formulated in stable form and can be administered topically in a cosmetic base with minimal irritant side effects. Further, when topically applied as taught by the invention, retinol causes effacement of facial fine lines and wrinkles, increases skin elasticity, reduces pore size and improves skin texture.

SUMMARY OF THE INVENTION

This invention relates to stable cosmetic compositions for reducing facial lines and wrinkles and otherwise enhancing skin quality and to methods of using that composition. The compositions comprise retinol coupled with a volatile silicone carrier by means of a mutual solvent. The preferred composition, which result in optimum stability and efficacy, are those containing volatile silicones, such as cyclomethicone, ethanol as the mutual solvent and retinol. When applied to the skin, the compositions contain 0.005 to 1.0 weight percent retinol. Most preferred compositions for application to the skin contain 0.01 to 0.50 weight percent retinol. The stable compositions of the invention may be formulated with more concentrated levels of retinol and may be diluted to suitable levels of retinol for application to the skin by means of cosmetically acceptable carriers. The compositions may additionally contain or may be applied in conjunction with a moisturizer to enhance the beneficial effects and sensory comfort of the composition.

DETAILED DESCRIPTION OF THE INVENTION

It has been discovered that a cosmetic composition containing retinol in a volatile silicone vehicle is stable, and upon topical application reduces fine lines and wrinkles and otherwise beneficially affects skin quality. More particularly, it has been discovered that a stable retinol composition can be formulated using a volatile silicone carrier and a mutual solvent for the silicone and retinol. Compositions containing 0.005 to 1.0 weight percent retinol can reduce facial fine lines and wrinkles with minimal irritant effects.

The stable retinol compositions of the invention are formulated in a vehicle containing a volatile silicone. With such a vehicle, retinol levels needed to achieve beneficial effects are minimized and the potential for irritant effects to the skin by retinol are greatly diminished. Moreover, retinol is stable when formulated in the silicone containing compositions of the invention, in contrast to other conventional cosmetic carriers.

The compositions of the invention may be formulated as alcohol lotions containing 0.005 to 1.0 weight percent retinol, in which case they may be applied directly to the skin, or as more concentrated alcohol lotions containing higher levels of retinol, in which case prior to application they are diluted by means of a cosmetically acceptable carrier to a 0.005 to 1.0 weight percent retinol level. In the formulations of the invention, water is optimally minimized or eliminated to maximize the stability of retinol and to minimize the potential for separation of the oil and water. No more than 2 percent water should be present.

When the compositions of the invention are formulated for application as alcohol lotions, a preferred mutual solvent for the volatile silicone and the retinol is ethanol. Preferred silicones are volatile low viscosity polysiloxanes, such as cyclomethicones, including cyclomethicone tetramer and pentamer. In the alcohol lotion formulation, the retinol level is most preferably 0.10 to 0.50 weight percent. The weight ratio of silicone to mutual solvent is optimally about 6:4.5 when cyclomethicone tetramer is the silicone and ethanol is the mutual solvent. At that level, stability, comfort and aesthetics are optimized. For stability the silicone should be at least 20 weight percent of the alcohol lotion composition. The ethanol or other mutual solvent, such as isopropyl alcohol, should be present in an amount sufficient to couple the silicone and retinol and yet not exceed the level at which tearing, stinging or other discomfort is observed. Generally, levels of ethanol between 25 to 60 weight percent will be acceptable.

An alcohol lotion composition may additionally contain emollients, and thickening agents for aesthetic effects such as lubrication and tactile perception. The emollients which may be present include all standard emollients which are miscible in the alcohol lotion. Preferred emollients include ethyl hexyl palmitate, neopentyl glycol dicaprate and ethylene glycol dicaprate. The quantity thereof is dependent upon tactile perception and compatibility with the silicone and solvent. Levels up to 15 weight percent will commonly be acceptable.

Ultraviolet absorbers or sunscreens, antioxidants and the like may also be present in the compositions of the invention to enhance the stability of retinol against degradation. Examples of ultraviolet absorbers which may be employed in the alcohol lotion formulation include octyl dimethyl PABA and benzophenone-3. Examples of suitable antioxidants and preservatives include butylated hydroxytoluene, BHA, imidazoline urea and methylparaben. Thickeners are those which are compatible with the overall composition, such as bentones, fumed silica and ethyl cellulose. Dyes, fragrance and other cosmetic additives may also be present, if desired, provided they do not react with any component of the composition and do not interfere with the homogeneity of the composition. The stable retinol/silicone compositions of the invention may be formulated in concentrated form, that is, may be formulated with higher levels of retinol, without loss of stability. However, when so formulated the compositions of the invention are diluted to produce retinol levels of 0.005 to 1.0 weight percent, preferably 0.01 to 0.50 weight percent, prior to application to the skin. In preferred practice, dilution may be effected by means of a water in oil emulsion. In such an emulsion, silicones of the type employed in the alcohol lotion are preferred. The silicone will commonly be 15 to 35 weight percent of the composition which is applied to the skin and most preferably about 20 weight percent of the composition.

A suitable emulsion for dilution of the compositions of the invention may be formed by first mixing the volatile silicones with silicone dimethicone copolyol. The remaining components of the emulsion, such as emulsifiers, emulsion stabilizers, preservatives and sunscreens, are dissolved or dispersed in water. The aqueous phase is then very slowly added to the cyclomethicone phase with vigorous homogenization which is continued until an acceptable viscosity is achieved.

The aqueous phase of the emulsion should contain preservatives of the type indicated for the alcohol lotion. It is also desirable that emulsion stabilizers, such as sodium chloride be employed.

The relative ratios of the water and oil phases is optimally 2 to 1. Deviations from this ratio result in changes in the viscosity of the system. The limits of permissible variation are dependent upon cosmetically acceptable viscosities.

When the composition of the invention is formulated in concentrated form for application in an emulsion of the type described, the emulsion and composition are blended prior to application. The quantity of emulsion employed is dependent on the concentration of the retinol composition of the invention. For example, if the retinol composition contains 4 weight percent retinol, sufficient emulsion must be added to reduce the percent weight of retinol to the 0.005 to 1.0 range, or more preferably to the 0.01 to 0.50 range.

The compositions of the invention, when formulated in concentrated form, can also be diluted to the appropriate retinol level for application by means of other cosmetically acceptable carriers or vehicles which are miscible with the retinol composition of the invention. Other cosmetic additives may be employed, either in the compositions of the invention or in those compositions when diluted with a suitable vehicle, provided they do not react with the retinol and are otherwise compatible with the compositions.

The compositions formulated as described above are topically applied to the skin on concentration which result in application of 0.005 to 1.0 weight percent retinol, preferably 0.01 to 0.50 weight percent. They are applied in the areas where fine lines, wrinkles, dry or inelastic skin or large pores are observed. Optimally a moisturizer is applied with or after application of the retinol compositions to enhance the tactile comfort associated with application of the compositions and to enhance the wrinkle effacement and other benefits achieved by the compositions.

Alternatively, it has been discovered that moisturizing efficacy can be achieved in the compositions of the present invention containing the retinol, thereby precluding the need for a separate moisturizer. Therefore, preferred compositions of the invention can be formulated in include moisturizing components that are compatible with the alcohol lotion or silicone emulsion to a level of up to 35% by weight of the final formulation. Preferred moisturizing ingredients suitable for use the preferred compositions of the invention may be selected from the group comprising gly acrylic polymer (Lubragel), petrolatum, ethylhexyl palmitate, and hyaluronic acid sodium salt.

With daily application, skin texture, color and tone will improve. Wrinkles and fine lines will be reduced with minimal irritant effects.

The following examples are illustrative of the invention and of the beneficial effects which can be achieved with the compositions of the invention and should not be construed as limiting.

EXAMPLE 1

A preferred alcohol lotion composition in accordance with the invention was formulated as follows (all quantities are stated as weight percents):

A retinoid blend was formulated containing:
48.01264: Polysorbate 20
48.01264: Retinol
3.00000: BHT
0.75000: BHA
0.09977: Retinol Acetate
0.09977: Retinol Palmitate
0.02494: Carotene
0.00024: Apocarotenal The blend was combined with an alcohol lotion composition to form the following composition of the invention:

| Formulation A | | |
|---|---|---|
| | 46.27776% | Cyclomethicone-Tetramer |
| | 35.00000% | Alcohol SD 40B Anhydrous |
| | 5.00000% | Ethylhexyl Palmitate |
| | 5.00000% | Octyl Dimethyl PABA |
| | 2.00000% | Benzophenone-3 |
| | 2.00000% | Demineralized Water |
| | 2.00000% | Neopentyl Glycol Dicaprate |
| | 1.50000% | Ethyl Cellulose K5000 |
| | 0.22000% | Butylated Hydroxytoluene |
| | 1.00224% | Retinoid Blend |
| Total | 100.00000% | |

EXAMPLE 2

A preferred emulsion was formulated as follows. A concentrated retinoid composition in accordance with the invention was formulated as follows:

| Retinoid Blend (Example 1) | 4.17600 |
|---|---|
| BHT | .16660 |
| Alcohol SD40B Anhydrous | 33.33330 |
| Cyclomethicone-Tetramer | 62.32410 |

A water in oil emulsion was formulated as follows:

| Cyclomethicone Tetramer | 11.36360 |
|---|---|
| Cyclomethicone Pentamer | 5.68180 |
| Cyclomethicone/Dimethicone Copolyol | 11.36360 |
| Demineralized Water | 64.91370 |
| Sodium Chloride | 1.13640 |
| Methylparaben | .45450 |
| Stearyl ETO (20 M) Alcohol | 1.13640 |
| Triethanolamine 99% | 1.25000 |
| Phenyl Benzimidazole | 2.27270 |
| BHT | .22730 |
| Germall (Sutton Laboratories) | .20000 |

Before application, the concentrated retinoid composition and the emulsion are blended to form the following composition suitable for application to the skin.

| Formulation B | |
|---|---|
| 57.12406% | Demineralized Water |
| 16.97770% | Cyclomethicone-Tetramer |
| 10.00000% | Cyclometh/dimeth Copolyol 90/10 |
| 5.00000% | Cyclomethicone-Pentamer |
| 4.00000% | Alcohol SD 40B Anhydrous |
| 2.00000% | Phenyl Benzimidazole-5-Sulf Acid |
| 1.10000% | Triethanolamine 99% |
| 1.00000% | Stearyl ETO (20 M) Alcohol |
| 1.00000% | Sodium Chloride |
| 0.40000% | Methylparaben |
| 0.22000% | Butylated Hydroxytoluene |
| 1.00224% | Retinoid Blend |
| 0.17600% | Germall |
| Total 100.00000% | |

EXAMPLE 3

A commercially available Vitamin A Alcohol Blend (Retinol Blend) was obtained comprising the following ingredients by percent weight:

| Polysorbate 20 | 48.125 |
|---|---|
| Retinol | 48.125 |
| BHT | 3.000 |
| BHA | 0.750 |
| | 100.000% |

This produced a composition which contained approximately 1.5 million units of Vitamin A activity per gram. This Retinol Blend or composition was used to prepare the following test formulations:

| | Alcohol Lotion | Emulsion |
|---|---|---|
| Alcohol SD 40B Anhydrous | 35.00000 | 4.00000 |
| Benzophenone-3 | 2.00000 | |
| Neopentyl Glycol Dicaprate | 2.00000 | |
| Demineralized Water | 2.00000 | 59.50000 |
| Ethylcellulose K5000 | 1.50000 | |
| Cyclomethicone-Tetramer | 45.50000 | 15.00000 |
| Ethyhexyl Palmitate | 5.00000 | |
| Octyl Dimethyl PABA | 5.00000 | |
| Fumed Silica | 1.00000 | |
| Cyclomethicone Pentamer | | |
| Cyclomethicone Dimethicone Copolyol | | 5.00000 |
| | | 10.00000 |
| Sodium Chloride | | 1.00000 |
| Methylparaben | | .40000 |
| Stearyl ETO (20 M) Alcohol | | 1.00000 |
| Triethanolamine 99% | | 1.10000 |
| Phenyl Benzamidazole | | 2.00000 |
| Vitamin A Alcohol Blend | 1.00000 | 1.00000 |

A split face test was conducted by using the foregoing following formulations as follows. Twelve females aged 20 to 59 applied one of the test formulations to one side of their faces and the other to the other side once daily for eight weeks. Rich Moisture Cream (Avon), a moisturizer, was applied over both retinol treated areas after application of the test formulation. Thin shavings of the skin on each side of the face were taken before the test began and after the eight week test period. It was observed that the skin shavings after the test were in better condition than those before the test in nine of the twelve women. The skin of those nine women was both thicker and more organized after the test than before. There were no observable differences between the effects of the two test formulations.

EXAMPLE 4

Rhino mouse skin studies were conducted to determine the effectiveness of retinol in normalizing epidermal skin structures. Rhino mice normally have wrinkled, sagging skin. The rhino mouse test is used as a model for showing the effects of compositions on the epidermis. In the test each set of seven mice was treated for five days/week for six consecutive weeks. Eight sets of mice were treated. The treating agents were similar to the vehicles of Formulations A and B in Examples 1 and 2 without the retinol blend and each of those vehicles with the retinol blend, with the retinol content at concentrations of 0.10, 0.25 and 0.50 weight percent. Specifically, the four silicone emulsions contained:

| | I | II | III | IV |
|---|---|---|---|---|
| Cyclomethicone-Pentamer | 5.00000 | 5.00000 | 5.00000 | 5.00000 |
| Cyclomethicone-Tetramer | 17.50000 | 16.97300 | 16.97300 | 16.97300 |
| Cyclometh/Dimeth Copolyol 90 | 10.00000 | 10.00000 | 10.00000 | 10.00000 |
| Demineralized Water | 59.50000 | 59.50000 | 59.50000 | 59.50000 |
| Sodium Chloride | 1.00000 | 1.00000 | 1.00000 | 1.00000 |
| Methylparaben | .40000 | .40000 | .40000 | .40000 |
| Stearyl ETO (20 M) Alcohol | 1.00000 | 1.00000 | 1.00000 | 1.00000 |
| Triethanolamine 99% | 1.10000 | 1.10000 | 1.10000 | 1.10000 |
| Phenyl Benzimidazole-5-Sulf. | 2.00000 | 2.00000 | 2.00000 | 2.00000 |
| Alcohol SD 40B Anhydrous | 2.50000 | 2.80000 | 2.50000 | 2.00000 |
| Vitamin A Alcohol Blend | — | .20000 | .50000 | 1.00000 |
| Carotenoid Solution | — | .02500 | .02500 | .02500 |
| Vitamin A Palmitate | — | .00100 | .00100 | .00100 |
| Vitamin A Acetate | — | .00100 | .00100 | .00100 |

The four alcohol lotion formulations contained:

| | V | VI | VII | VIII |
|---|---|---|---|---|
| Alcohol SD 40B Anhydrous | 35.00000 | 35.30000 | 35.00000 | 35.50000 |
| Ethylhexyl Palmitate | 5.00000 | 5.00000 | 5.00000 | 5.00000 |
| Benzophenone-3 | 2.00000 | 2.00000 | 2.00000 | 2.00000 |
| Octyl Dimethyl PABA | 5.00000 | 5.00000 | 5.00000 | 5.00000 |
| Neopentyl Glycol Dicaprate | 2.00000 | 2.00000 | 2.00000 | 2.00000 |

-continued

|  | V | VI | VII | VIII |
|---|---|---|---|---|
| Demineralized Water | 2.00000 | 2.00000 | 2.00000 | 2.00000 |
| Ethyl Cellulose K5000 | 1.50000 | 1.50000 | 1.50000 | 1.50000 |
| Butylated Hydroxytoluene | .20000 | .22000 | .22000 | .22000 |
| Cyclomethicone-Tetramer | 46.30000 | 45.75300 | 45.75300 | 45.75300 |
| Silica-Fumed | 1.00000 | 1.00000 | 1.00000 | 1.00000 |
| Carotenoid Solution | — | .02500 | .02500 | .02500 |
| Vitamin A Acetate | — | .00100 | .00100 | .00100 |
| Vitamin A Palmitate | — | .00100 | .00100 | .00100 |
| Vitamin A Alcohol Blend | — | .20000 | .50000 | 1.00000 |

Visual observation of the skin condition during the period of treatment showed a diminution of the characteristic epidermal glandular structures in the sets of mice treated with formulations containing retinol. No such change in wrinkling and sagging was observed in the mice treated with the vehicle alone.

EXAMPLE 5

A test of the effectiveness of retinol formulations of the invention in reducing damage to skin resulting from exposure to sunlight, and more particularly ultraviolet wavelengths thereof, was conducted. The test was conducted using hairless mice. Sixty mice were exposed three days a week for ten weeks to 20 minutes of ultraviolet light. Thereafter the mice were divided into four groups of 5 mice each. Each group was treated with one of the four following compositions:

| Emulsion | | |
|---|---|---|
| Cyclomethicone Pentamer | 5.00000 | 5.00000 |
| Cyclomethicone Tetramer | 16.97300 | 17.50000 |
| Cyclometh/Dimeth Copolyol | 10.00000 | 10.00000 |
| Demineralized Water | 59.50000 | 59.50000 |
| Sodium Chloride | 1.00000 | 1.00000 |
| Methylparaben | .40000 | .40000 |
| Stearyl ETO (20 M) Alcohol | 1.00000 | 1.00000 |
| Triethanolamine 99% | 1.10000 | 1.10000 |
| Phenyl Benzimidazole | 2.00000 | 2.00000 |
| Alcohol SD 40B Anhydrous | 2.00000 | 2.50000 |
| Vitamin A Alcohol Blend | 1.00000 | |
| Carotenoid Solution | | .02500 |
| Vitamin A Palmitate | | .00100 |
| Vitamin A Acetate | | .00100 |
| Alcohol Lotion | | |
| Alcohol SD 40B Anhydrous | 34.50000 | 35.00000 |
| Ethylhexyl Palmitate | 5.00000 | 5.00000 |
| Benzophenone-3 | 2.00000 | 2.00000 |
| Octyl Dimethyl PABA | 5.00000 | 5.00000 |
| Neopentyl Glycol Dicaprate | 2.00000 | 2.00000 |
| Demineralized Water | 2.00000 | 2.00000 |
| Ethyl Cellulose K5000 | 1.50000 | 1.50000 |
| BHT | .22000 | .20000 |
| Cyclomethicone Tetramer | 45.75300 | 46.30000 |
| Fumed Silica | 1.00000 | 1.00000 |
| Carotenoid Solution | .02500 | |
| Vitamin A Acetate | .00100 | |
| Vitamin A Palmitate | .00100 | |
| Vitamin A Alcohol Blend | 1.00000 | |

Treatment was effected daily for five weeks. Another four groups of seven mice each were similarly treated for ten weeks.

After treatment, the skin repair of the UV-induced damage was observed. The skin of mice treated with retinol-containing formulations had up to a twofold greater repair zone than the skin of mice treated with either vehicle. This greater repair can be correlated with visual improvement in the skin. That is, under similar treatment with retinol, the human skin can be expected to show a diminution in lines and wrinkles.

EXAMPLE 6

A six month study was conducted to determine the ability of retinol to produce visible effacement of facial crowsfeet, lines and wrinkles and textural skin improvements. The test was done on a split face basis with half of the test population applying Formulation C and the other half using Formulation D:

| Cyclomethicone-Tetramer | 15.00000 | 45.30000 |
|---|---|---|
| Cyclomethicone-Pentamer | 5.00000 | — |
| Cyclomethy/Dimeth Copolyol 90/10 | 10.00000 | — |
| Dimineralized Water | 59.50000 | 2.00000 |
| Sodium Chloride | 1.00000 | — |
| Methylparaben | .40000 | — |
| Stearyl ETO (20 M) Alcohol | 1.00000 | — |
| Triethanolamine 99% | 1.10000 | — |
| Phenyl Benzimidazole-5-Sulf Acid | 2.00000 | — |
| Alcohol SD 40B Anhydrous | 4.00000 | 35.00000 |
| Vitamin A Alcohol Blend | 1.00000 | 1.00000 |
| Butylated Hydroxytoluene | — | .20000 |
| Ethylhexyl Palmitate | — | 5.00000 |
| Benzophenone-3 | — | 2.00000 |
| Octyl Dimethyl PABA | — | 5.00000 |
| Neopentyl Glycol Dicaprate | — | 2.00000 |
| Ethyl Cellulose K5000 | — | 1.50000 |
| Silica-Fumed | — | 1.00000 |

Crowsfeet, suborbital areas, cheeks and lips were treated. Application was done once a day.

Within two months of commencement of the test, the benefits of the retinol formulations were evident. Textural skin improvement was observed in the crowsfeet and cheek areas of the panelists. A softening or smoothing in fine lines in the crowsfeet and suborbital areas was also noted.

At the end of three months, line reduction in the crowsfeet and suborbital area appeared in more panelists than at the end of two month period. There was also a greater improvement in skin texture in the crowsfeet and cheek areas between the 2- and 3-month observations. Further, textural improvement in the suborbit of the eye and decreased dryness in the crowsfeet, suborbital and cheek areas were apparent.

After four months of treatment, the skin areas treated with the formulations of the invention showed marked improvement. Skin dryness and texture had improved in all four treated areas. Lines and wrinkles had diminished in the crowsfeet suborbital and cheek areas. The skin in the crowsfeet and suborbital areas also showed a significant improvement in firmness.

By the end of six months of treatment, the benefits of the formulations of the invention were fully apparent. With the exception of the lip area, there was a visual improvement in the treated skin's texture and the treated skin was significantly smoother to the touch. There had also been a significant reduction in the number of fine lines and/or wrinkles in the crowsfeet and suborbital regions and to a lesser extent on the cheeks.

EXAMPLE 7

A water in oil emulsion in accordance with the invention was formulated as follows:

|  | % |
|---|---|
| Volatile Silicone Tetramer | 15.0 |
| Volatile Silicone Pentamer | 5.0 |
| Dimethicone Copolyol | 10.0 |
| Water | q.s. |
| Eusolex 232 | 2.0 |
| TEA 99% | 1.1 |
| Sodium Chloride | 1.0 |
| Ethanol | 4.0 |
| Retinoid Blend 1.5 MM units (Example 1) | 1.0 |
| Bridge 78 (20) ethoxylated Stearyl Ether | 1.0 |

This product possesses excellent aesthetic properties and the retinol is acceptably stable in this vehicle over the intended usage period. Its efficacy has been established via the Rhino mouse test described in Example 4.

EXAMPLE 8

The stability of retinol in the compositions of the invention was tested. The formulations tested were as follows:

| Formulation C | |
|---|---|
| Cyclomethicone-Tetramer | 58.1481 |
| Anhydrous Alcohol | 33.3333 |
| Retinoid Blend | 8.3520 |
| BHT | 0.1666 |
|  | 100.0000% |

| Formulation D | |
|---|---|
| Cyclomethicone-Tetramer | 45.500 |
| Anhydrous Alcohol | 35.000 |
| Ethylhexyl Palmitate | 5.000 |
| Octyl Dimethyl PABA | 5.000 |
| Benzophenone-3 | 2.000 |
| Neopentyl Dicaprate | 2.000 |
| Demineralized Water | 2.000 |
| ECK-5000 | 1.500 |
| Retinol Blend | 1.000 |
| Fumed Silica | 1.000 |
|  | 100.000% |

| Formulation E | |
|---|---|
| Cyclomethicone-Tetramer | 39.80 |
| Anhydrous Alcohol | 40.00 |
| Retinoid Blend | 10.00 |
| BHT | 0.20 |
|  | 100.00 |

| Formulation F | |
|---|---|
| Cyclomethicone-Tetramer | 69.53 |
| Anhydrous Alcohol | 20.00 |
| Retinol Blend | 10.00 |
| BHT | 0.20 |
| Carotinoid-Solution | 0.25 |
| Retinyl Palmitate | 0.01 |
| Retinyl Acetate | 0.01 |
|  | 100.00% |

| Formulation G | |
|---|---|
| Cyclomethicone-Tetramer | 34.765 |
| Ethylhexyl Palmitate | 25.000 |
| Octyl Dimethyl PABA | 25.000 |
| Anhydrous Alcohol | 10.000 |
| Retinol Blend | 5.000 |
| Carotinoid Solution | 0.125 |
| BHT | 0.100 |
| Retinyl Palmitate | 0.005 |
| Retinyl Acetate | 0.005 |
|  | 100.000% |

| Formulation H | |
|---|---|
| Anhydrous Alcohol | 56.00 |
| Cyclomethicone-Tetramer | 22.00 |
| Octyl Dimethyl PABA | 8.00 |
| Ethylhexyl Palmitate | 5.00 |
| Benzophenone-3 | 3.00 |
| Neopentyl Dicaprate | 2.00 |
| Demineralized Water | 2.00 |
| Hydroxypropyl Cellulose | 1.30 |
| Retinol Blend | 0.50 |
| BHT | 0.20 |
|  | 100.00% |

| Formulation I | |
|---|---|
| Anhydrous Alcohol | 55.50 |
| Cyclomethicone-Tetramer | 22.00 |
| Octyl Dimethyl PABA | 8.00 |
| Ethylhexyl Palmitate | 5.00 |
| Benzophenone-3 | 3.00 |
| Neopentyl Dicaprate | 2.00 |
| Demineralized Water | 2.00 |
| Hydroxypropyl Cellulose | 1.30 |
| Retinol Blend | 1.00 |
| BHT | 0.20 |
|  | 100.00% |

The retinol blend used in the foregoing formulations was the same as the Vitamin A Alcohol Blend of Example 3, namely:

| Polysorbate 20 | 48.125 |
|---|---|
| Retinol | 48.125 |
| BHT | 3.000 |
| BHA | 0.750 |
|  | 100.000% |

The retinoid blend used in the foregoing formulations was as follows:

| Polysorbate 20 | 48.01264 |
|---|---|
| Retinol | 48.01264 |
| BHT | 3.00000 |
| BHA | 0.75000 |
| Retinyl Palmitate | 0.09977 |
| Retinyl Acetate | 0.09977 |
| Carotene | 0.02494 |
| Apocarotenal | 0.00024 |
|  | 100.00000% |

The Carotinoid Solution was as follows:

| Ethylhexyl Palmitate | 98.988 |
|---|---|
| Beta-Carotene | 1.000 |
| Canthaxanthine | 0.002 |
| Apocarotenal | 0.010 |
|  | 100.000% |

The results were as follows:

| Week | C | D | E | F | G | H | I |
|---|---|---|---|---|---|---|---|
| 100° F. Formulation | | | | | | | |
| 0 | — | — | — | — | — | — | — |
| 1 | — | 92% | 99% | 94% | 103% | 104% | 102% |
| 2 | 99% | 88% | 98% | 97% | 103% | 110% | 98% |
| 3 | 102% | 81% | — | — | — | — | — |
| 4 | 100% | — | — | 97% | 104% | 108% | 87% |
| 6 | 101% | 80% | 98% | 93% | 100% | — | — |
| 8 | 97% | 79% | — | 89% | 95% | 94% | 95% |
| 12 | — | 82% | 93% | 89% | 97% | 87% | 94% |
| Room Temperature | | | | | | | |

-continued

| Week | C | D | E | F | G | H | I |
|---|---|---|---|---|---|---|---|
| | | | Formulation | | | | |
| 0 | 100% | 100% | 100% | 100% | 100% | 100% | 100% |
| 1 | — | — | — | — | — | 108% | 100% |
| 2 | — | 101% | — | — | — | 112% | 101% |
| 3 | 102% | 94% | — | — | — | — | — |
| 4 | 101% | — | — | — | — | 104% | 99% |
| 6 | 100% | 98% | — | — | — | — | — |
| 8 | 99% | 96% | — | — | — | 106% | 104% |
| 12 | 99% | 87% | 98% | 96% | 101% | 102% | 99% |

EXAMPLE 9

An alternatively preferred emulsion was formulated by forming a composition in accordance with the invention as follows:

| | |
|---|---|
| Retinoid Blend (Example 1) | 0.1740 |
| BHT | 0.1666 |
| Alcohol SD40B Anhydrous | 33.3333 |
| Cyclomethicone-Tetramer | 66.3238 |
| Beta-Carotene | 0.0023 |

A water-in-oil emulsion was formulated as follows:

| | |
|---|---|
| Cyclomethicone-Tetramer | 7.38560 |
| Cyclomethicone-Pentamer | 3.97800 |
| Cyclometh/Dimeth Copolyol 90/10 | 11.36360 |
| Petrolatum | 5.68180 |
| Ethylhexyl Palmitate | 5.68180 |
| Demineralized Water | 36.15350 |
| Sodium Chloride | 1.13640 |
| Methylparaben | 0.45450 |
| Stearyl ETO (20 M) Alcohol | 1.13640 |
| Gly Acrylic Polymer (Lubragel) | 22.72730 |
| Hyaluronic Acid Sod. Salt | 0.05110 |
| Triethanolamine 99% | 1.55000 |
| Phenyl Benzimidazole-5-Sulf Acid | 2.27270 |
| Butylated Hydroxytoluene | 0.22730 |
| Germall | 0.20000 |

As in prior examples, before application, the concentrated retinol composition and the emulsion were blended together to form the following composition suitable for topical application to the skin.

| Formulation J | |
|---|---|
| Demineralized Water | 31.81508 |
| Gly Acrylic Polymer (Lubragel) | 20.00020 |
| Cyclomethicone-Tetramer | 14.45792 |
| Cyclometh/Dimeth Copolyol) 90/10 | 10.00000 |
| Cyclomethicone-Pentamer | 3.50064 |
| Petrolatum | 5.00000 |
| Ethylhexyl Palmitate | 5.00000 |
| Alcohol SD 40B Anhydrous | 4.00000 |
| Phenyl Benzimidazole-5-Sulf Acid | 2.00000 |
| Triethanolamine 99% | 1.36400 |
| Stearyl ETO (20 M) Alcohol | 1.00000 |
| Sodium Chloride | 1.00000 |
| Hyaluronic Acid Sod. Salt | 0.04500 |
| Methylparaben | 0.40000 |
| Butylated Hydroxytoluene | 0.22000 |
| Retinoid Blend (Example I) | 0.02088 |
| Germall | 0.17600 |
| Beta-Carotene | 0.00028 |
| | 100.00000% |

It will be noted that this composition (Formulation J) and that of Example 10 below includes moisturizing ingredients such as gly acrylic polymer (Lubragel), petrolatum, ethylhexyl palmitate, and hyaluronic acid sodium salt.

EXAMPLE 10

A split face test was conducted using the following emulsion formulation:

| | |
|---|---|
| Demineralized Water | 32.07848 |
| Gly Acrylic Polymer (Lubragel) | 20.00020 |
| Cyclomethicone-Tetramer | 14.45852 |
| Cyclometh/Dimeth Copolyol 90/10 | 10.00000 |
| Cyclomethicone-Pentamer | 3.50064 |
| Petrolatum | 5.00000 |
| Ethlhexyl Palmitate | 5.00000 |
| Alcohol SD 40B Anhydrous | 4.00000 |
| Phenyl Benzimidazole-5-Sulf Acid | 2.00000 |
| Triethanolamine 99% | 1.10000 |
| Stearyl ETO (20 M) Alcohol | 1.00000 |
| Sodium Chloride | 1.00000 |
| Hyaluronic Acid Sod. Salt | .04500 |
| Methylparaben | .40000 |
| Butylated Hydroxytoluene | .22000 |
| Retinoid Blend (Example I) | .02088 |
| Germall | .17600 |
| Beta-Carotene | .00028 |

Sixteen females aged 30-54 applied the test formulation to one side of their face twice daily for six weeks, the other side remained untreated. A leading clinical dermatologist observed a significant reduction in the appearance of the signs of facial aging including: diminution of skin lines and an improvement in the look and feel (texture) of facial skin.

EXAMPLE 11

The panelists who participated in the study in Example 10 were instrumentally assessed for improvement in facial lines via digital image processing of skin surface replicas (Image Analysis) and by Optical Profilometry, a measure of the degree of skin surface smoothness. After 6 weeks of product usage, there was a 26% reduction in skin lines as measured by Image Analysis, and there was a 41% improvement in skin smoothness as shown by Optical Profilometry.

EXAMPLE 12

The ability of an electric current to flow through the stratum corneum provides an indirect measurement of the corneum's water content. The panelists who participated in the study in Example 10 were assessed for moisturization using an IBS impedance/conductance meter. At least twelve hours elapsed between the last product application and the skin conductance measurement. The data clearly showed that the treated side was more moist (higher conductance readings at all measurement time points). Further, the untreated control side of the face decreased in relative moisture content while the test side increased. Thus, the objective measurement and substantiation of the stratum corneum's electrical conductivity showed a significant enhancement in facial skin moisture content.

EXAMPLE 13

The effectiveness of Formulation J in Example 9 on Skin biomechanical properties was evaluated by the in-vivo extensometer. One forearm site of thirteen panelists and one leg site from 10 panelists were treated with the composition of Formulation J. The contralateral forearm or leg respectively served as the untreated control. Both single and multiple applications were measured for a usage period of up to seven days. The results from this study indicated a product induced change in the skin's biomechanical properties. There was a 36% improvement in skin extensibility/elasticity immediately after product application, a 26% improvement for up to three hours after multiple product application. All these values were statistically significant.

EXAMPLE 14

A test of the ability of a retinol containing composition to enhance the rate of cellular turnover in the epidermis was conducted. The human epidermis represents a cell renewal system in which fully differentiated cells (corneocytes) are being continually shed from the skin surface. Since this system operates under steady-state conditions, this loss of desquamated cells must be balanced by new cell production in the germinative cell layers. One parameter that is especially important to measure in such a system is transit time—the time required for a cell to move through a compartment. Since cells move in unison as a layer through the stratum corneum, this means, in this special case, that transit time is equivalent to turnover time—the time required for a compartment to completely renew itself.

Previous studies have shown that the turnover time of the stratum corneum can be measured nointrusively by impregnating it with a fluorescent marker dye that binds avidly to the nonviable corneocytes but not the underlying viable epidermal cells. Thus, the time required for the dye to disappear, which can be monitored by Wood's lamp examination, is an indication of the turnover time of the stratum corneum. Therefore, any difference in the time required for the dye to disappear from a treated and a nontreated site can be considered to be an expression of that product's ability to enhance epidermal renewal.

A test of fifteen healthy female subjects aged 25–45 participated in the study. One arm site was untreated, the other was treated with a composition according to the present invention comprising:

| | |
|---|---|
| Dimineralized Water | 32.08388 |
| Gly Acrylic Polymer (Lubragel) | 20.00020 |
| Cyclomethicone-Tetramer | 14.45852 |
| Cyclometh/Dimeth Copolyol 90/10 | 10.00000 |
| Cyclomethicone-Pentamer | 3.50064 |
| Petrolatum | 5.00000 |
| Ethylhexyl Palmitate | 5.00000 |
| Alcohol SD 40B Anhydrous | 4.00000 |
| Phenyl Benzimidazole-5-Sulf Acid | 2.00000 |
| Triethanolamine 99% | 1.10000 |
| Stearyl ETO (20 M) Alcohol | 1.00000 |
| Sodium Chloride | 1.00000 |
| Hyaluronic Acid Sod. Salt | .03960 |
| Methylparaben | .40000 |
| Butylated Hydroxytoluene | .22000 |
| Retinoid Blend (Example I) | .02088 |
| Germall | .17600 |
| Beta-Carotene | .00028 |

A two week pretreatment was conducted during which time the composition was applied to the test site twice daily (excluding the weekends). Dansyl chloride stain was then administered to both the treated and untreated sites. This was followed by a 3–5 week period during which the twice daily application of the present composition to the treated site was continued.

The results of this study indicated that the test product enhanced epidermal cell renewal by approximately 25% over no treatment.

EXAMPLE 15

A test of the retinol containing composition of Example 14 to induce retinoid benefits to the skin was conducted. The composition (Example 14) was applied to the upper inner arm of ten women aged 25–45 twice daily for a seven week period. Superficial shave biopsies of the epidermis were taken from the treated site and from an adjacent untreated control area. Histological observations for retinoid effects were made by a leading clinical dermatologist.

The results of this study indicated that retinoid effects were observed in 30% of the panelists. These effects included improvement in vertical orientation and cellular stacking in the epidermis and slight increase in the size of the cells. Further, 20% of the panelists demonstrated an increase in viable epidermis thickness.

EXAMPLE 16

Rhino mouse skin studies were conducted to determine the effectiveness of retinol in normalizing epidermal skin structures. Rhino mice normally have wrinkled, sagging skin. The rhino mouse test is used as a model for showing the effects of compositions on the epidermis. In the test each set of seven mice was treated for five days/week for six consecutive weeks. Five sets of mice were treated. The treating agents were simlar to the vehicles of formulation J in Example 9 without the retinol blend and that vehicle with the retinol blend, with the retinol content at concentrations of 0.005, 0.01, and 0.03 weight percent. Specifically, the four silicone emulsions contained:

| | I | II | III | IV |
|---|---|---|---|---|
| Demineralized Water | 32.08388 | 32.08388 | 32.08388 | 32.08388 |
| Gly Acrylic Polymer (Lubragel) | 20.00020 | 20.00020 | 20.00020 | 20.00020 |
| Cyclomethicone-Tetramer | 14.44968 | 14.45852 | 14.41955 | 14.46924 |
| Cyclometh/Dimeth CoPolyol 90/10 | 10.00000 | 10.00000 | 10.00000 | 10.00000 |
| Cyclomethicone-Pentamer | 3.50064 | 3.50064 | 3.50064 | 3.50064 |
| Pentrolatum | 5.00000 | 5.00000 | 5.00000 | 5.00000 |
| Ethylhexyl Palmitate | 5.00000 | 5.00000 | 5.00000 | 5.00000 |
| Alcohol SD 40B Anhydrous | 4.00000 | 4.00000 | 4.00000 | 4.00000 |
| Phenyl Benzimidazole-5-Sulf Acid | 2.00000 | 2.00000 | 2.00000 | 2.00000 |
| Triethanolamine 99% | 1.10000 | 1.10000 | 1.10000 | 1.10000 |
| Stearyl ETO (20 M) Alcohol | 1.00000 | 1.00000 | 1.00000 | 1.00000 |
| Sodium Chloride | 1.00000 | 1.00000 | 1.00000 | 1.00000 |
| Hyaluronic Acid Sod. Salt | .03960 | .03960 | .03960 | .03960 |
| Methylparaben | .40000 | .40000 | .40000 | .40000 |

-continued

|  | I | II | III | IV |
|---|---|---|---|---|
| Butylated Hydroxytoluene | .22000 | .22000 | .22000 | .22000 |
| POE (20 M) Sorbitan Monomaurate | .03000 | — | — | — |
| Germall | .17600 | .17600 | .17600 | .17600 |
| Retinoid Blend (Example I) | — | .02088 | .06013 | .01044 |
| Beta-Carotene | — | .00028 | — | — |

Visual observation of the skin condition during the period of treatment showed significant diminution of the characteristic epidermal utriculi and an increase in viable epidermal thickness in the sets of mice treated with the present formulations containing retinol when compared with the sets of mice either untreated or treated with the vehicle alone.

EXAMPLE 17

A test of the effectiveness of the formulation in Example 14 to visibly reduce tiny dry facial lines in the crowsfeet areas was conducted to assess its moisturizing ability. Twenty-eight women who were prescreened for lines in the crowsfeet area participated in the study. Panelists applied the test product twice daily for at least two weeks to only one side of the face and left the other side untreated to serve as the control site. After application of the composition of Example 14, a trained evaluator, who had no knowledge of the treatment side, rated the panelist's lines on both sides of the face. The results of this study indicated that there was a statistically significant visual improvement in the number and depth of fine dry lines after just seven days application of the test product.

EXAMPLE 18

A test of the ability of the composition of Example 14 to reduce skin dryness was conducted. Twelve panelists who demonstrated skin dryness upon repeated soap washing of the hands were selected to participate in this study. Initially, the panelists induced a condition of dryness by washing their hands with bar soap. The test product was applied daily to one hand while the other was left untreated to serve as a control side. Each hand was rated randomly by two trained evaluators who had no knowledge of which hand had been treated. The evaluators used a stereomicroscope to assist them with their ratings. The results of this study revealed that effective moisturization benefits were demonstrated throughout treatment by the composition of Example 14. In addition, these benefits persisted for twenty-four hours after the final treatment indicating that the test product provides effective long-lasting moisturization.

It will thus be appreciated that moisturizing efficacy can be achieved with the compositions of the present invention containing the retinol, thereby precluding the need for a separate moisturizer. Therefore, preferred compositions of the invention can be formulated to include moisturizing components that are compatible with the alcohol lotion or silicone emulsion to a level of up to 35% by weight of the final formulation.

Many modifications of the present invention will be apparent to those skilled in the art. Accordingly, the present invention should be limited only by the spirit and scope of the present claims.

We claim:

1. A method of reducing skin wrinkles comprising the following steps:
   (a) providing a stable cosmetic composition comprising retinol in an amount ranging from 0.005 to 1.0 percent by weight, a volatile silicone in an amount ranging from 15 to 35 percent by weight, and a mutual solvent for the retinol and the volatile silicone in an amount ranging from 25 to 60 percent by weight, and
   (b) topically applying to the skin an effective wrinkle reducing amount of the above stable composition.

2. The method of claim 1 wherein the volatile silicone is cyclomethicone.

3. The method of claim 1 wherein the mutual solvent is ethanol.

4. The method of claim 1 wherein the weight ratio of silicone to mutual solvent is 6:4.5.

5. The method of claim 1 further comprising: up to 15 weight percent emollient.

6. The method of claim 1 said stable composition containing 0.01 to 0.50 weight percent retinol.

7. The method of claim 1 wherein said stable composition further comprises a cosmetically acceptable vehicle in an amount sufficient to reduce the level of retinol to between 0.005 and 1.0 weight percent and wherein the vehicle is a water in oil emulsion.

8. The method of claim 7 wherein the weight ratio of the oil phase to the water phase is about 1:2.

9. The method of claim 1 further comprising applying a skin moisturizer to the skin at substantially the same time as the stable composition is applied.

10. The method of claim 9 wherein said moisturizing ingredient is selected from the class comprising gly acrylic polymer, petrolatum, ethylhexyl palmitate, and hyaluronic acid sodium salt.

* * * * *